United States Patent
Marrelli et al.

[11] Patent Number: 6,128,962
[45] Date of Patent: Oct. 10, 2000

[54] THREE-PHASE FLUID FLOW MEASUREMENT SYSTEM AND METHOD

[75] Inventors: John D. Marrelli; Frank M. Rexach, both of Houston, Tex.

[73] Assignee: Texaco Inc., White Plains, N.Y.

[21] Appl. No.: 09/186,437

[22] Filed: Nov. 5, 1998

Related U.S. Application Data

[63] Continuation of application No. 08/901,110, Jul. 28, 1997, abandoned.

[51] Int. Cl.⁷ ................................ G01F 1/74; G01V 3/18
[52] U.S. Cl. ........................................ 73/861.04; 324/638
[58] Field of Search ........................... 73/861.04, 152.18, 73/61.1 R, 861.07; 324/638

[56] References Cited

U.S. PATENT DOCUMENTS

| | | |
|---|---|---|
| 4,852,395 | 8/1989 | Kolpak . |
| 4,881,412 | 11/1989 | Northedge . |
| 5,127,272 | 7/1992 | Dean et al. . |
| 5,234,012 | 8/1993 | Marrelli . |
| 5,535,632 | 7/1996 | Kolpak . |
| 5,576,974 | 11/1996 | Marrelli et al. . |
| 5,597,961 | 1/1997 | Marrelli . |
| 5,625,293 | 4/1997 | Marrelli et al. . |
| 5,654,502 | 8/1997 | Dutton . |
| 5,763,794 | 6/1998 | Marrelli . |

*Primary Examiner*—William Oen
*Assistant Examiner*—Abdallahi Aw-musse
*Attorney, Agent, or Firm*—Morris N. Reinisch; Howrey Simon Arnold & White

[57] ABSTRACT

Method and apparatus for three-phase fluid flow measurement that operates reliably and accurately over a wide range of gas cut. The system uses a fluid conditioner to separate the three-phase fluid flow into a liquid rich component and a gas rich component. The gas flow rate of the gas rich component is controlled by a valve to maintain the gas cut at a predetermined level. The valve is responsive to control signals generated by a measurement apparatus that measures oil, gas, and water cuts. The system configuration includes a pipeline for carrying the liquid rich component, a gas line for carrying the gas rich component, and a measurement line in parallel with the pipeline.

17 Claims, 2 Drawing Sheets

6,128,962

THREE-PHASE FLUID FLOW MEASUREMENT SYSTEM AND METHOD

CROSS-REFERENCE TO RELATED APPLICATION

The present application is a continuation of Application No. 08/901,110, filed Jul. 28, 1997 now abandoned, the entirety of which is herein incorporated by reference.

BACKGROUND OF THE INVENTION

I. Field of the Invention

The present invention relates to multi-phase fluid flow measurement, and more particularly, to a system and method for three-phase fluid flow rate measurement.

II. Description of the Related Art

Generally, oil, gas and water simultaneously flow from a producing well. A production mixture of oil, gas and water is often referred to as a three-phase flow of oil, gas and water. The term "phase", as used herein, refers to a type of fluid that may exist in contact with other fluids. A mixture of oil and water, for example, includes a discrete oil phase and a discrete water phase. Similarly, a mixture of oil, gas and water includes a discrete gas phase and a discrete liquid phase, with the liquid phase including an oil phase and a water phase.

It is often necessary to measure the oil, gas and water flow rates, $Q_o$, $Q_g$ and $Q_w$, respectively, of a three-phase fluid flow. The ratios or fractions of oil, gas and water of a three-phase fluid flow are referred to in the industry as oil, gas, and water cuts, respectively.

Consider a three-phase fluid flow in a pipeline composed of oil, water and gas phases.

The oil, water and gas flow rates in the pipeline are at the respective rates of $Q_o$, $Q_w$, and $Q_g$. Suppose, at any point along the axial length of the pipeline, the volumetric fractions of oil, water and gas are $X_o$, $X_w$, and $X_g$, respectively. The volumetric fractions are represented by the following equations.

$$X_o + X_w + X_g = 1 \quad (1)$$

$$\text{Water Cut } W_c = X_w / (X_o + X_w) \quad (2)$$

$$\text{Oil Cut } O_c = 1 - W_c \quad (3)$$

$$\text{Gas Cut } G_c = X_g / (X_o + X_w) \quad (4)$$

$$\text{Gas Volume Fraction GVF} = Q_g / (Q_g + Q_o + Q_w) \quad (5)$$

The flow rates and volumetric fractions are related by the following equations.

$$X_o = Q_o / (Q_w + Q_o) \quad (6)$$

$$X_w = Q_w / (Q_w + Q_o) \quad (7)$$

$$X_g = Q_g / (Q_w + Q_o) \quad (8)$$

Multi-phase fluid flow measurement systems, also known as multi-phase fluid flow meters (MPMs), are used to measure $Q_o$, $Q_g$ and $Q_w$ of a three-phase fluid flow. Three types of MPMs differing in degree of fluid separation are generally available: three-phase separation MPM; two-phase separation MPM; and no-separation MPM. Conventional threephase and two-phase separation MPMs often suffer from the disadvantages of large size and poor accuracy. They often require large separators to substantially separate the gas component from the liquid component of a multi-phase fluid flow. A separator completely separates a multi-phase fluid into its respective phases such water, oil and gas, or simply liquids and gas.

Industry terminology refers to a "two-phase" separator as one that is used to separate a gas phase from a liquid phase including oil and water. The output streams of a two-phase separator are a liquid stream in a liquid leg and a gas stream in a gas leg. A three-phase separator is used to separate the gas phase from the liquid phase and also separates the liquid phase into oil and water phases. The output streams of a three-phase separator are an oil stream in an oil leg, a water stream in a water leg and a gas stream in a gas leg. Each stream may be represented by a fluid rate and a fluid fraction.

As compared to two-phase separators, three phase separators require additional valves and other assemblies. Also, three-phase separators typically have larger volumes to permit longer residence times of produced materials for gravity separation of the production materials into their respective oil, gas and water components.

As noted before, conventional MPMs require large separators to substantially separate the liquid and gas components of the multi-phase fluid flow. Without a substantial separation of the liquid and gas components, conventional systems do not accurately measure the water, oil and gas cuts of the multi-phase fluid flow. A large separator, however, adds size and weight to the overall system, thereby making it less desirable in some locations.

Additionally, some conventional no-separation MPMs measure the various ratios accurately only if the gas cut is within a preferred range. One system, for example, operates reliably if the gas cut is between 60%–70%. Others operate satisfactorily provided that the gas cut is between 70–85%. Thus, most conventional systems are either too large or are not very reliable over a wide range of gas cut.

For these reasons, there is a need for a MPM that is accurate and reliable over a wide range of gas cut. Furthermore, there is a need for a MPM that is smaller in size compared to a conventional system.

SUMMARY OF THE INVENTION

The present invention is directed to a system and a method for measuring oil, gas and water flow rates of a three-phase fluid flow. Oil, gas and water cuts can be readily calculated from oil, water and gas flow rates. In one embodiment of the invention, the method comprises the steps of receiving the three-phase fluid in a fluid conditioner, wherein the liquid rich component with small amounts of gas (liquid rich stream) of the three-phase fluid flows downwardly exiting the fluid conditioner via a pipe called the liquid leg, and the gas rich component with small amounts of liquid (gas rich stream) of the three phase fluid rises upwardly exiting the fluid conditioner via a pipe called the gas leg.

The method further comprises drawing a sample stream from the liquid rich stream, determining the oil, gas and water cuts of the liquid rich stream, generating control signals corresponding to the oil, gas and water cuts, and adjusting a valve in the gas leg using the control signals so that the gas cut of the liquid rich stream is at a predetermined level, such as less than 5%, less than 20%, or between 60 and 70%, or between 70 and 85%, or greater than 90%, thereby increasing the accuracy of the measurement of the rates.

The method further comprises the steps of carrying the gas rich stream by the gas leg, adjusting the valve to control the gas flow rate through the gas leg, measuring the gas flow rate by a gas meter, and releasing the gas rich stream back to the pipeline to join the liquid rich stream.

In one embodiment of the present invention, the system for measuring the oil, gas and water rates and cuts of a three-phase fluid flow comprises means for determining the oil, gas and water rates and cuts of a three-phase fluid flow, means for generating control signals corresponding to the oil, gas and water cuts, and means for adjusting a valve using the control signals so that the gas cut of the liquid rich stream is at a predetermined level, thereby increasing the accuracy of the measurement of the rates.

The system further comprises means for receiving the three-phase fluid wherein the liquid rich component of the three-phase fluid flows downwardly and the gas rich component of the three-phase fluid rises upwardly, means for carrying the liquid rich component, and means for drawing a sample stream from the liquid rich component and directing the sample stream through a measurement apparatus.

The system further comprises means for carrying the gas rich stream of the three-phase fluid flow, means for controlling the gas flow rate, means for measuring the gas flow rate, and means for releasing the gas rich stream back to the liquid component.

BRIEF DESCRIPTION OF THE DRAWINGS

In the drawings, like reference numbers generally indicate identical, functionally similar, and/or structurally similar elements. The drawing in which an element first appears is indicated by the leftmost digit(s) in the reference number.

The present invention will be described with reference to the accompanying drawings, wherein.

DETAILED DESCRIPTION OF THE PREFERRED EMBODIMENTS

I. Overview

The present invention is directed to a system and a method for multi-phase fluid flow measurement. More specifically, the present invention is a system and method for three-phase fluid flow measurement, which measures the oil rate ($Q_o$), the oil fraction ($X_o$), the gas rate ($Q_g$), the gas fraction ($X_g$), the water rate ($Q_w$), and the water fraction ($X_w$) of a three-phase fluid flow. The cuts, fractions and rates are all interelated by the preceeding nomenclatures and definitions.

Although the present invention readily finds application in the oil and gas industry where three-phase fluid flow situations are often encountered, the utility of the present invention is not limited to the oil and gas industry. In fact, it will become apparent to one skilled in the art that the concept of the present invention will find utility in other areas as well.

The present invention offers numerous advantages over conventional three-phase fluid flow measurement systems. Most significant among the advantages are a substantial reduction in size, an improvement in accuracy of the three-phase fluid flow measurement system, and an increase in the range of flow rates which can be accurately measured.

The present invention improves the accuracy of $Q_o$, $Q_w$, and $Q_g$ measurements by controlling the gas fraction in the liquid leg ($X_{gl}$). According to the present invention, the oil, gas, and water fractions in the liquid leg, $X_{ol}$, $X_{gl}$ and $X_{wl}$, respectively, are determined by a measurement apparatus, and control signals representing $X_o$, $X_{gl}$ and $X_{wl}$ are generated. The control signals are then used to adjust the position of a valve that controls $X_{gl}$ in the liquid leg of three-phase fluid flow. Stated in another way, the present invention uses feed-back control methods to accurately measure $Q_o$, $Q_w$, and $Q_l$ by controlling $X_{gl}$ in the liquid rich stream in the liquid leg of a two phase separator.

The present invention reduces the overall size and weight of the three-phase fluid measurement system by eliminating the need for a large separator. The present invention does not require a complete separation of the liquid and gas components of the three-phase fluid flow. In fact, the present invention can be designed to operate reliably over a wide range of $X_g$. The present invention, for example, can be designed to operate accurately where $X_g$ is less than 5% or 20%. Alternatively, the present invention can be designed to operate accurately where, for example, $X_g$ is between 60%–70%, between 70%–85%, or between 90%–100%.

Figure 1:
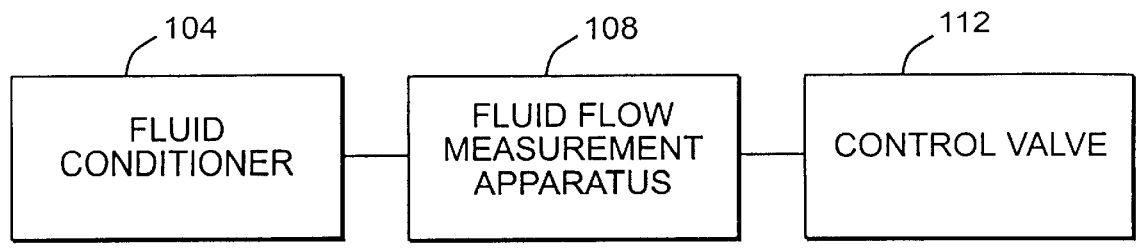
FIG. 1 is a high-level block diagram of the invention.

Briefly stated, the present invention comprises three main elements: (a) a fluid conditioner; (b) a measurement apparatus; and (c) a valve. FIG. 1 is a block diagram of the invention illustrating a fluid conditioner 104, a measurement apparatus 108 and a valve 112. The measurement apparatus 108 determines the following:

$Q_{ol}$=oil flow rate in the liquid leg;
$Q_{wl}$=water flow rate in the liquid leg;
$Q_{gl}$=gas flow rate in the liquid leg;
$X_{ol}$=oil fraction in the liquid leg;
$X_{wl}$=water fraction in the liquid leg;
$X_{gl}$=gas fraction in the liquid leg;
$Q_{og}$=oil flow rate in the gas leg;
$Q_{wg}$=water flow rate in the gas leg;
$Q_{gg}$=gas flow rate in the gas leg;
$X_{og}$=oil fraction in the gas leg;
$X_{wg}$=water fraction in the gas leg; and
$X_{gg}$=gas fraction in the gas leg.

The valve 112 controls the pressure in the fluid conditioner 104 and thereby controls $X_{gl}$.

II. System Description

Figure 2:
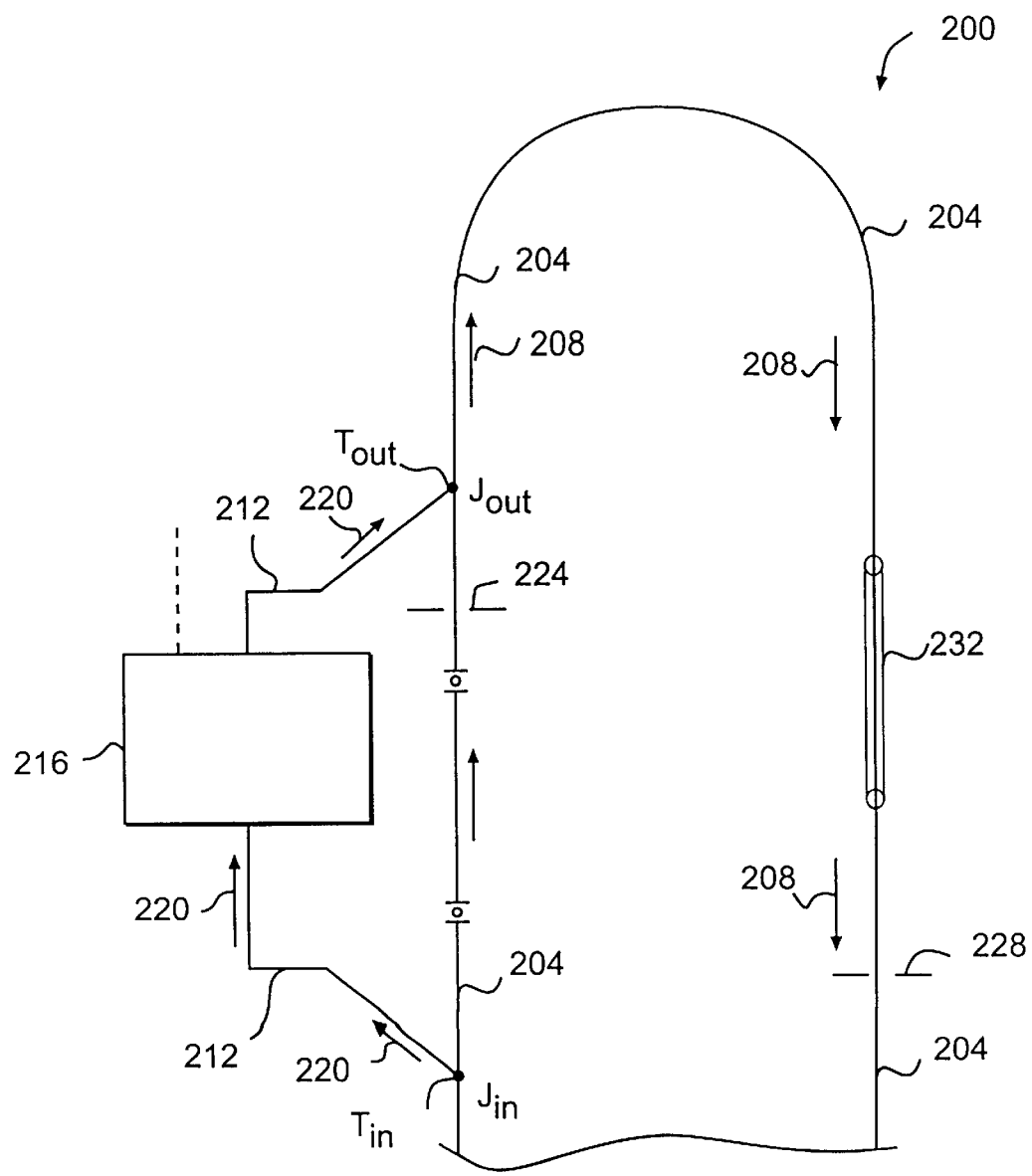
FIG. 2 illustrates a three-phase fluid flow measurement system employing the concepts of the present invention.

Referring initially to FIG. 2, a three-phase fluid flow measurement system 200 employing the concepts of the present invention is shown schematically. While the present invention is described in conjunction with the three-phase fluid flow (i.e., oil, gas and water), it should be understood that the present invention can be adapted for use in a fluid flow having more than three phases.

Referring again to FIG. 2, a pipeline 204, bent into an inverted U-shape as substantially shown, carries fluid in the direction of flow arrows 208. A measurement line 212 is connected in parallel to a segment of the pipeline 204. The measurement line 212 draws a sample stream from the pipeline 204 at $T_{in}$ and releases the sample stream back to the pipeline 204 at $T_{out}$. The diameter of the measurement line 212 is smaller than the diameter of the pipeline 204. The measurement line 212 directs the sample stream through a measurement apparatus 216. Fluid flow in the measurement line 212 is in the direction of flow arrows 220.

It has been known that measurement accuracy is enhanced if the sample stream velocity in the measurement apparatus 216 is the same as that through the pipeline 204. This principle is known as isokinetic sampling. Accordingly, a first orifice 224 causes a pressure drop in the measurement line 212 which causes the measurement line 212 to have the same fluid velocity as the pipeline 204. A second orifice 228 restores the pressure of the fluid flow.

Inside the measurement apparatus 216, the sample stream is directed through bends that interrupt the flow pattern of the fluid. To restore the flow pattern, a flow straightener 232 is connected in series with the pipeline 204 downstream of the measurement apparatus The measurement apparatus 216 determines $Q_o$, $Q_w$, $Q_g$, $X_o$, $X_g$, and $X_w$ of the fluid flow. The measurement apparatus 216 generates control signals that correspond to the measured ratios or fractions. The control signals are then used to adjust the position of an adjustable valve. Position of the adjustable valve controls the upstream pressure in pipeline 204 and therefore the gas fraction $X_g$. The operation of the measurement apparatus 216 will be described subsequently.

Figure 3:
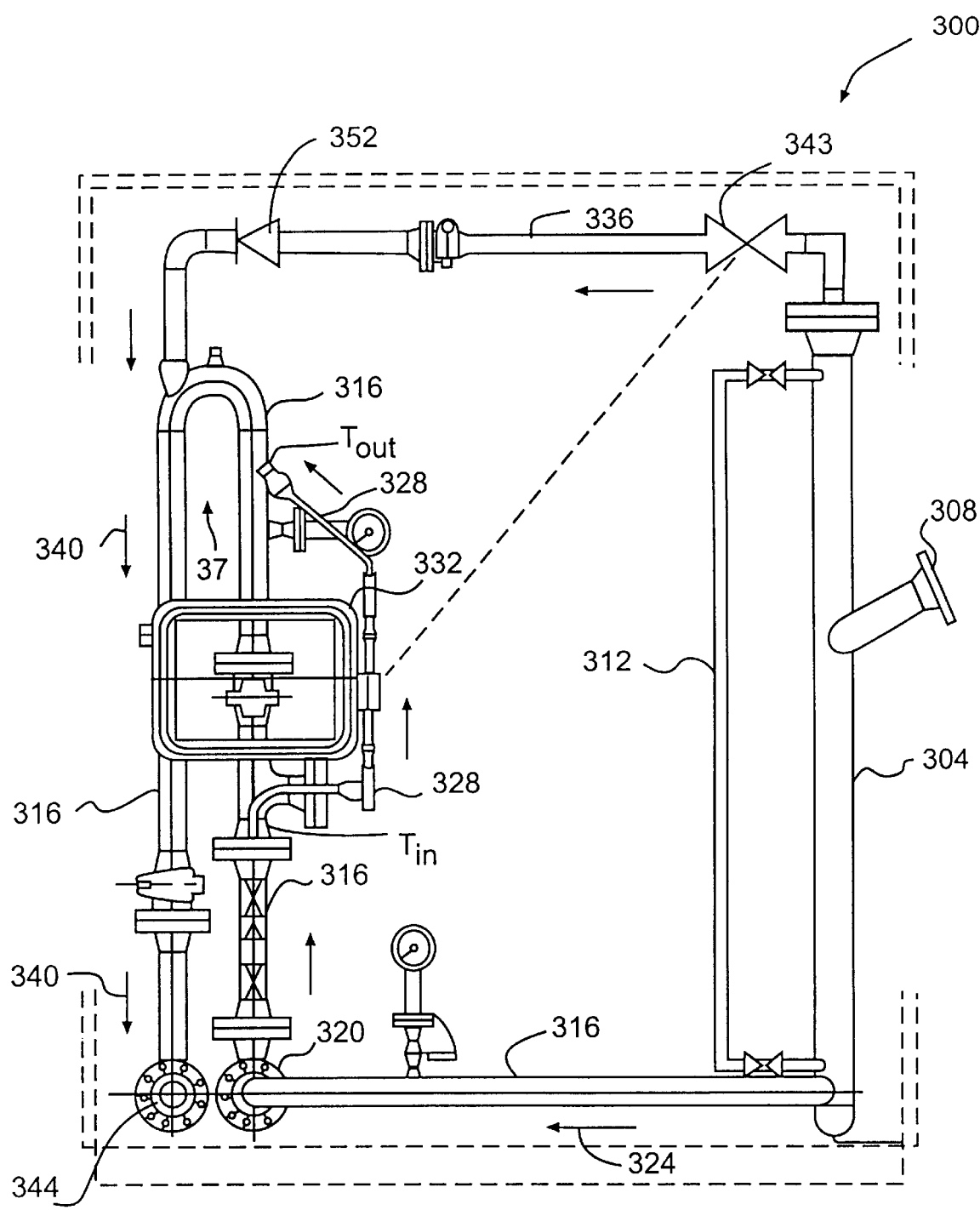
FIG. 3 is a three-phase fluid flow measurement system in accordance with one embodiment of the present invention.

Reference is now made to FIG. 3, which shows a three-phase fluid measurement system 300 in accordance with one embodiment of the present invention. A cylindrical fluid conditioner 304 receives fluid through an input flange 308. In one embodiment, the fluid conditioner 304 is secured in a vertical position. Alternatively, the fluid conditioner 304 can be inclined at a selected angle.

The fluid is a mixture of a liquid component and a gas component. The liquid component primarily comprises oil and water. The liquid component, however, may include between 0% to 90% gas.

As the fluid enters the fluid conditioner 304, it forms a vortex, with the liquid component flowing downwardly towards the bottom of the fluid conditioner 304 and the gas component rising upwardly towards the top of the fluid conditioner 304. A level gauge 312 connected in parallel to the fluid conditioner 304 measures gas and liquid levels in the fluid conditioner 304.

A pipeline 316 extends horizontally from the bottom of the fluid conditioner 304. In one embodiment, the pipeline 316 then bends at a substantially right angle at a flange 320. The pipeline 316 then forms an inverted U-shaped section as shown in FIG. 3. The pipeline 316 finally exits the fluid flow measurement system 300 at a flange 344. It should, however, be understood that the pipeline 316 may have other shapes besides as shown in FIG. 3.

The liquid component flows through the horizontal section of the pipeline 316 in the direction of the flow arrow 324. The liquid component then enters the inverted U-shaped section of the pipeline 316.

A measurement line 328 is connected in parallel to a leg of the inverted U-shaped section of the pipeline 316. A sample stream is drawn through the measurement line 328 at $T_{in}$. The sample stream is passed through a measurement apparatus 332 that measures $X_{ol}$, $X_{gl}$ and $X_{wl}$ of the fluid flow. The sample stream is released back to the pipeline 316 at $T_{out}$.

A gas line 336 carries the gas component from the top of the fluid conditioner 304 and releases it back to the pipeline 316. The rejoined gas component and the liquid component flow in the direction of the flow arrow 340 and finally exit the system 300 at the flange 344.

Note that the measurement apparatus 332 measures $X_{ol}$, $X_{gl}$ and $X_{wl}$ of the fluid flow through the measurement line 328. Since the sample stream is a representative sample of the fluid flow through the pipeline 316, the measured ratios fairly represent the oil, gas and water cuts through the pipeline 316. However, $X_{gl}$ does not represent the total gas cut $X_{gt}$ of the fluid entering the fluid conditioner 304 at the input flange 308, because a portion of $X_{gt}$ is bypassed the pipeline 316 and is carried instead by the gas line 336. The total gas rate $Q_{gt}$ and gas cut $X_{gt}$ of the fluid flow entering the fluid conditioner 304 can be determined mathematically from $Q_{ol}$, $Q_{wl}$, $Q_{gl}$, $X_{ol}$, $X_{gl}$, $X_{wl}$, and the flow rate of gas through the gas line 336.

In the gas line 336, the gas component passes through a valve 348 and a gas meter 352. The valve 348 is an adjustable type that controls the gas flow rate through the gas line 336. In one embodiment, the opening and closing of the valve 348 is controlled by a dc signal. For example, a dc signal that varies between 0–10 volts can be used to control the valve position. In one embodiment, the dc signal sets $X_{gl}$. When the dc signal is at 0 volt, the valve 348 is completely closed, and when the dc signal is at 10 volts, the valve 348 is completely opened.

Closing the valve 348 increases the amount of gas in the fluid conditioner 304. Consequently, the liquid level in the fluid conditioner 304 drops, and more gas is forced through the pipeline 316 and eventually through measurement apparatus 332. Thus, closing the valve 348 increases $X_{gl}$. On the other hand, opening the valve 348 decreases the amount of gas in the fluid conditioner 304. This raises the liquid level in the fluid conditioner 304, thereby decreasing $X_{gl}$. The gas meter 352 measures the gas flow rate through the gas line 336.

The measurement apparatus 332 produces control signals corresponding to the measured fractions. The control signals are then used to control the position of the valve 348.

The measurement apparatus 332 can be one of several types available in the industry. One such measurement apparatus 332 is known as the STARCUT™(registered trademark of Texaco Inc.) monitor system. The STARCUT™ monitor system is described in U.S. Pat. Nos. 5,625,293 and 5,234,012. These U.S. patents are incorporated herein by reference in their entirety for all purposes. Another measurement apparatus is described in U.S. Pat. No. 5,127,272, which is also incorporated herein in its entirety for all purposes.

The accuracy of the measurement apparatus 332 is important to the determination of $X_{ol}$, $X_{gl}$ and $X_{wl}$. Generally, the accuracy of a particular type of measurement apparatus varies with $X_{gl}$ of the fluid. The present invention can be adapted for use with most available measurement apparatus. The STARCUT™ monitor system, for example, operates reliably when $X_{gl}$ is less than or equal to 20%. If the STARCUT™ monitor system is selected as the measurement apparatus, the adjustable valve 348 is positioned so that $X_{gl}$ is within the allowable range. The MPM described in U.S. Pat. No. 5,127,272, on the other hand, measures $Q_o$, $Q_w$, and $Q_g$, and operates reliably when $X_{gl}$ is between 60%–70%. In that case, the adjustable valve must be positioned so that $X_{gl}$ is within the allowable range of 60%–70%.

The present invention significantly reduces the size of the three-phase fluid flow measurement system. In the present invention, a substantial separation of the liquid component from the gas component is not necessary for accurate measurements. Consequently, a large three-phase separator is unnecessary. The present invention can be designed to operate reliably under a wide range of $X_g$, e.g., between 0%–99%. The fluid conditioner 304 and the valve 348 maintain a desired value of $X_{gl}$ in the pipeline 316. Stated in another way, the combination of the fluid conditioner 304 and the valve 348 replaces a large three-phase separator.

While various embodiments of the present invention have been described above, it should be understood that they have been presented by way of example only, and not limitation. Thus, the breadth and scope of the present invention should not be limited by any of the above-described exemplary embodiments, but should be defined only in accordance with the following claims and their equivalents.

What is claimed is:

1. A method for multi-phase fluid flow measurement, comprising the steps of:

determining an oil, a gas and a water cut of a three-phase fluid flow;

generating control signals corresponding to the oil, gas and water cuts;

measuring an oil, a gas and a water rate of the three-phase fluid flow; and adjusting a valve using the control signals so that the gas cut of the three-phase fluid flow is at a predetermined level, thereby increasing the accuracy of the measurement of the rates.

2. The method according to claim 1, further comprising the steps of:

receiving the three-phase fluid in a fluid conditioner wherein the liquid rich component of the three-phase fluid flows downwardly and the gas rich component of the three phase fluid rises upwardly in the fluid conditioner;

carrying the liquid rich component in a pipeline connected to the fluid conditioner; and drawing a sample stream from the pipeline and directing the sample stream through a measurement apparatus.

3. The method according to claim 2, further comprising the steps of:

carrying the gas rich component of the three-phase fluid flow by a gas line;

adjusting the valve to control the gas flow rate through the gas line;

measuring the gas flow rate by a gas meter; and releasing the gas rich component back to the pipeline to join the liquid component.

4. The method according to claim 3, wherein the valve is disposed in the gas line.

5. The method according to claim 1, wherein the predetermined level of the gas cut is less than 20%.

6. A system for multi-phase fluid flow measurement, comprising:

means for determining an oil, a gas and a water cut of a three-phase fluid flow;

means for generating control signals corresponding to the oil, gas and water cuts;

means for measuring an oil, a gas and a water rate of the three-phase fluid flow; and means for adjusting a valve using the control signals so that the gas cut of the three-phase fluid flow is at a predetermined level, thereby increasing the accuracy of the measurement of the rates.

7. The system according to claim 6, further comprising:

means for receiving the three-phase fluid, wherein the liquid rich component of the three-phase fluid flows downwardly and the gas rich component of the three phase fluid rises upwardly;

means for carrying the liquid rich component; and means for drawing a sample stream from the liquid rich component and directing the sample stream through a measurement apparatus.

8. The system according to claim 7, further comprising:

means for carrying the gas rich component of the three-phase fluid flow;

means for controlling the gas flow rate;

means for measuring the gas flow rate; and means for releasing the gas rich component back to the liquid component.

9. The system according to claim 6, wherein the predetermined level of the gas cut is 20%.

10. The system according to claim 6, wherein the valve is disposed in a gas line that carries the gas rich component of the three-phase fluid flow.

11. A three-phase fluid flow meter for measuring the oil, gas and water cuts of a three-phase fluid flow, comprising:

a fluid conditioner adapted to receive the three-phase fluid flow, wherein the liquid rich component of the three-phase fluid flows downwardly and the gas rich component of the three-phase fluid flows upwardly;

a pipeline for carrying the liquid rich component from the fluid conditioner;

a gas line for carrying the gas rich component from the fluid conditioner and releasing back to the pipeline;

a measurement line connected in parallel to the pipeline;

a measurement apparatus that determines the oil, gas and water cuts of the three-phase fluid flow and that generates control signals corresponding to the oil, gas and water cuts, the measurement line drawing a sample stream from the pipeline and directing the sample stream through the measurement apparatus; and a valve for controlling the gas flow rate through the gas line, wherein the valve is responsive to the control signals so that the gas cut in the pipeline is at a predetermined level.

12. The fluid flow meter according to claim 11, further comprising a level gauge connected in parallel to the fluid conditioner for monitoring liquid and gas levels in the fluid conditioner.

13. The fluid flow meter according to claim 11, further comprising a gas meter for measuring the gas flow rate through the gas line.

14. The fluid flow meter according to claim 11, wherein the predetermined level of the gas cut is 20%.

15. The fluid flow meter according to claim 11, wherein the pipeline comprises a substantially horizontal portion and an inverted U-shaped portion.

16. The fluid flow meter according to claim 15, wherein the inverted U-shaped portion comprises a first leg and a second leg, and wherein the measurement line is connected in parallel to one of the first and second legs.

17. The fluid flow meter according to claim 11, wherein the valve is disposed in the gas line.

* * * * *